United States Patent [19]

Walters et al.

[11] Patent Number: 5,136,110
[45] Date of Patent: Aug. 4, 1992

[54] PROCESS FOR THE PREPARATION OF BISPHENOLS

[75] Inventors: Marlin E. Walters, West Columbia; W. Frank Richey; Emmett L. Tasset, both of Lake Jackson, all of Tex.

[73] Assignee: The Dow Chemical Company, Midland, Mich.

[21] Appl. No.: 626,597

[22] Filed: Dec. 12, 1990

Related U.S. Application Data

[63] Continuation-in-part of Ser. No. 472,508, Jan. 29, 1990, abandoned.

[51] Int. Cl.$^5$ .................. C07C 37/18; C07C 39/12
[52] U.S. Cl. ........................ 568/722; 568/717; 568/723; 568/726
[58] Field of Search ............... 568/722, 727, 723, 718, 568/717, 726

[56] References Cited

U.S. PATENT DOCUMENTS

| | | | |
|---|---|---|---|
| 2,634,297 | 4/1953 | Moyle | 568/718 |
| 2,858,342 | 10/1958 | Bender et al. | 568/718 |
| 3,001,972 | 9/1961 | Christenson et al. | 568/718 |
| 3,378,518 | 4/1968 | Doyle | 568/718 |
| 4,467,122 | 8/1984 | Szabolcs | 568/718 |

FOREIGN PATENT DOCUMENTS

| | | | |
|---|---|---|---|
| 0259746 | 8/1987 | European Pat. Off. | |
| 1092027 | 3/1958 | Fed. Rep. of Germany | 568/718 |
| 2919757 | 5/1979 | Fed. Rep. of Germany | |
| 1296024 | 12/1986 | Japan | 568/718 |
| 885005 | 12/1961 | United Kingdom | 568/718 |
| 894620 | 4/1962 | United Kingdom | 568/718 |
| 935061 | 8/1963 | United Kingdom | 568/718 |

OTHER PUBLICATIONS

Justus Liebig's Annalen der chemie 363: pp. 275-276 (1908).
Chemical Abstract 29:855(7) (1935).
Chemical Abstract 65:3795c (1966).
J. Amer. Chem. Soc. 37, pp. 2575-2591 (1915).
Chemical Abstract 85:192405k (Japan Kokai 76 86,434).
J. Amer. Chem. Soc. 61, pp. 345-348 (1939).
J. Amer. Chem. Soc. 76, pp. 4547-4550 (1954).

*Primary Examiner*—Werren B. Lone

[57] ABSTRACT

The invention is a process for the preparation of triaromatic bisphenols reacting a phenolic compound, e.g. phenol, with a suitable halo-compound, for instance 1,1-dichloroethylbenzene, 1-chlorostyrene, or mixtures thereof. The reaction may be conducted in the presence or absence of a solvent; an excess of the phenolic compound can serve as the solvent. The product is conveniently recovered by removing the by-product HCl, excess phenolic compound, excess solvent and cooling. Yields of bis-1,1-(4-hydroxyphenyl)-1-phenylethane which are greater than 90% of theoretical have been obtained by the reaction of phenol and 1,1-dichloroethylbenzene and a large portion of the yield is para isomer. Suitable halo-compounds include aromatic dihalo-compounds having at least one aliphatic substituent having two alpha-halogen atoms and at least one beta halogen atom, halo-styrenes having structures corresponding to such aromatic dihalo-compounds except that an alpha-halogen atom and a beta hydrogen atom are removed and there is a double bond between the alpha and beta carbon atoms, trihalotoluenes, and dihalocyanotoluenes.

28 Claims, No Drawings

PROCESS FOR THE PREPARATION OF BISPHENOLS

CROSS-REFERENCE TO RELATED APPLICATION

This application is a continuation-in-part of application serial number 472,508, filed Jan. 29, 1990, now abandoned.

BACKGROUND OF THE INVENTION

This invention relates to preparation of bisphenols, particularly bisphenols having a carbon atom having bonded thereto an aliphatic group and at least three aromatic groups, at least two of which aromatic groups each have at least one phenolic group, hereinafter referred to as triaromatic bisphenols. Bisphenols are the building block molecules for such materials as polycarbonates, epoxy resins, polysulfones, polyarylates and the like. Bisphenols in which the phenolic rings are joined together through a single bridging carbon are usually manufactured by condensing two moles of phenol with an aldehyde or a ketone in the presence of an acid catalyst. Bisphenol A is the most commonly used bisphenol and is made from the reaction of acetone with phenol. Because it must be performed under mild temperature conditions (50-70° C.) to minimize the formation of undesirable coproducts, it is a slow reaction. Other bisphenols are employed to impart specific properties to the above resins. Some of these properties are, for example, toughness, strength, better thermal properties and solvent resistance. Bisphenol AP, the bisphenol of phenol and acetophenone (bis-1,1-(4-hydroxyphenyl)-1-phenylethane), is known to improve the thermal properties of polycarbonates, polyarylates and epoxy resins over similar materials made from bisphenol A.

The condensation of phenol with acetophenone, however, is very slow. Even with zinc chloride as a catalyst, the reaction requires two days to complete (U.S. Pat. No. 4,467,122). Then an extended work-up must be performed to remove as much residual zinc salts as possible. With HCl as the catalyst, the reaction requires 10-14 days. These process limitations, along with the lack of commercially significant quantities of acetophenone, have hindered the development of useful applications for Bisphenol AP. A more facile process should allow wider use of this valuable monomer.

In order to achieve the high molecular weights required to produce the desired thermal and mechanical properties, the bisphenol starting materials for such thermoplastics as polycarbonates and polyarylates preferably have the constituent phenol groups substituted in the para position in greater than 98% selectivity. Although most of the ortho-substituted material can be separated by crystallization, it is most desirable for good process economics to minimize the product containing any ortho isomer. In one reference, J. American Chemical Society, 76, 4547(1954)], 1-chloroethylbenzene is reported to react with phenol to give a mixture of isomers of 1-(hydroxyphenyl)-1-phenylethane having the hydroxy group of the phenyl group in the ortho and para position in a mole ratio of 55 ortho to 45 para position.

It would be desirable to prepare triaromatic bisphenols more quickly than is typical for condensations of acetophenone with phenols and to prepare them such that there is a high selectivity for the para isomer. Bishydroxyphenyl compounds, including triaromatic bisphenols, are preferably in the para isomer form (having the hydroxy group on the phenyl ring para to the attachment of the phenyl ring to the carbon atom to which the other phenyl group(s) are attached) because such isomers result in high polymers with desirable properties of high molecular weight, impact strength, modulus and the like.

SUMMARY OF THE INVENTION

Bisphenols are made by reacting a halo-compound which is (1) a trihalotoluene, (2) a dihalocyanotoluene, (3) an aromatic dihalo-compound having at least one aliphatic substituent having two alpha-halogen substituents and at least one beta hydrogen atom, (4) a corresponding halo-styrene or (5) mixtures thereof with a phenolic compound. At least two moles of the phenolic compound per mole of halo-compound are preferably employed. The reaction may be conducted with or without a solvent. The bisphenol is conveniently recovered by removing by-product HCl, excess phenolic compound and solvent (if any) and cooling to obtain the product. Alternatively, a crystallization solvent is used.

In contrast with conventional technology, the new method is rapid and uses a simple purification to give the desired product. For instance, yields of bis-1,1-(4-hydroxyphenyl)-1-phenylethane (Bisphenol AP) of up to 95 percent of theoretical can be obtained using this process.

The reaction is broadly applicable with other aromatic hydroxy compounds such as naphthols and substituted phenols which can be reacted with the halo-compounds in place of phenol to prepare analogous bis hydroxyaromatic derivatives.

There is advantageously high selectivity for the para isomers. For instance, we have now discovered that under mild conditions, the reaction of phenol with 1,1-dichloroethylbenzene (DCEB) will produce bisphenol AP rapidly with excellent selectivity to the p,p' isomer, preferably with greater than 94% selectivity. This selectivity is unexpected in view of the known art.

DETAILED DESCRIPTION OF THE INVENTION

The process of the invention is represented by the reaction:

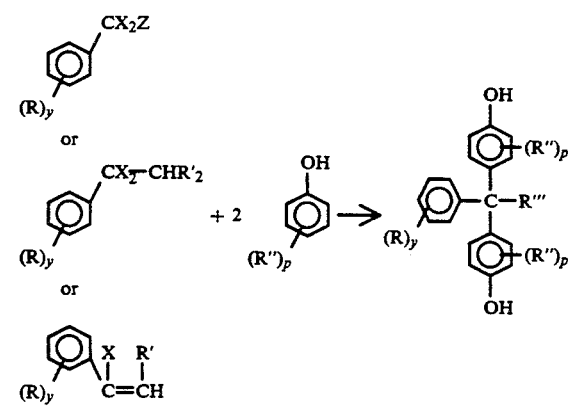

wherein each R' is independently H or an aliphatic group; each R, or R" is independently an inert substituent or an aliphatic or aromatic group wherein two or more R's and/or 2 or more R"'s are optionally joined to form cycloaliphatic or aromatic groups; R''' is CN or (R'')p-phenyl-OH in the case of the $-CX_2Z$ starting material, $-CHR'_2$ in the case of the dihalo starting material or $-CH_2R'$ in the case of the halostyrene starting material; X is a halogen, either chlorine or bromine, preferably chlorine; Z is a chlorine, bromine or a cyano group (CN); y is an integer of from 0 to 5, preferably from 0 to about 2, more preferably from 0 to 1; p is an integer of from 0 to 4, preferably from 0 to about 2, most preferably from 0 to 1. When R' is an aliphatic group, each R' preferably has from 1 to about 15 carbon atoms, more preferably from 1 to about 5 carbon atoms. Each aliphatic R, R' or R'' is unsubstituted or optionally inertly substituted. By inert substituent or inertly substituted it is meant that the substituent is one which does not undesirably interfere with the reaction of the aromatic halo-compound with a phenolic compound. Compounds wherein R''' is (R'') P-phenyl-OH are referred to herein as tris-[1,1,1-(H$_2$hydroxyphenyl)] toluenes and are new compounds useful in making polymers.

In the illustrated reaction sequence, the compounds having X substituents are those referred to herein as halo-compounds. The halo-compounds include dihalo alkyl aromatic compounds having an aliphatic substituent, said substituent having two alpha-halogen atoms (attached to an alpha carbon atom which is attached to an aromatic ring) and at least one beta hydrogen atom (attached to a beta carbon atom which is attached to the alpha carbon atom having the halogen atoms), optionally inertly substituted trihalotoluenes and cyanodihalotoluenes, and halo-styrene compounds corresponding to the dihalo alkyl aromatic compounds in structure except that one halogen atom and the beta hydrogen atom are eliminated and a double bond is present between the alpha and beta carbon atoms. Either type of halo-compound is suitable for use in the practice of the invention. Suitable halo-compounds include 1-chlorostyrene; 1,1-dichloroethylbenzene (DCEB); 1-bromostyrene; 1,1-dibromoethylbenzene; 1,1-dichloro-n-hexylbenzene; 1,1,1-trichlorotoluene; 1,1,1-tribromotoluene; o-methyl-1,1,1-trichlorotoluene; 1-cyano-1,1-dichlorotoluene; m-ethyl-1,1,1-trichlorotoluene and the like and mixtures thereof. Preferred compounds are 1-chlorostyrene, 1,1-dichloroethylbenzene and mixtures thereof. Such compounds wherein all the halogen atoms are chlorine are referred to herein as chloro-compounds.

The process of the present invention can be illustrated by the process for making bis-1,1-(4-hydroxyphenyl)-1-phenylethane (Bisphenol AP) by contacting (a) 1,1-dichloroethylbenzene or 1-chlorostyrene or a mixture thereof, with (b) phenol, wherein the phenol is preferably present in an amount equivalent to at least a two molar multiple of the amount of (a) present. Reactants are preferably in liquid form. For instance, the halo-compound can be employed as a neat liquid and the phenol can be in its molten form or either one or both reactants can be dissolved in an inert solvent prior to contacting. After the reaction is desirably complete, the product bisphenol is recovered. For instance, the reaction mixture can be cooled to effect crystallization of the product bisphenol.

Any method of recovery within the skill in the art is suitable. An alternative method of recovering the product is to remove the unreacted phenolic compound, the HCl produced in the reaction and solvent (if any) prior to cooling to effect the crystallization of the bisphenol. Yet another way of recovering the product is to remove most of the unreacted phenolic compound, then to add a solvent and cool to effect the crystallization of the bisphenol.

Although the reaction is autocatalytic because the HCl produced by the reaction is an effective catalyst, any strong acid catalyst, advantageously HCl or any other hydrogen halide, may be added to the phenol as a catalyst for the reaction, preferably before the addition of the halo-compound because addition of the acid catalyst is more useful before the concentration of HCl produced in the reaction has reached a desired catalytic concentration. It is advantageous to conduct the reaction under a pressure greater than atmospheric by the use of a hydrogen halide, e.g. hydrogen chloride. The pressure of the hydrogen halide may vary from about 1 to about 100 atmospheres, preferably from about 1 to about 10 atmospheres.

Triaromatic bisphenols (analogous to Bisphenol AP), can be prepared from aromatic hydroxyl compounds (any phenolic or thiophenolic compound which reacts with the halo-compound) such as naphthols, hydroxybiphenyl substituted phenols and the like by reacting them with the halo-compounds. Thus, for example, naphthols, hydroxybiphenyls, alkylphenols, dialkylphenols thiophenols, nitrophenols and halophenols can be employed in place of the phenol reactant in the process. Specific hydroxyaromatic compounds useful in the reaction include o- and m-cresols, 2,6-dimethyl-phenol, nonylphenol, o- and m-chlorophenols, 2-naphthol, 1-naphthol, ethylphenol, 2-methylthiophenol, resorcinol, 2-nitrophenol, 3-nitrophenol, 2-chloro-thiophenol and the like. Preferred compounds include alkyl phenolic having alkyl groups of from 0 to about 5 carbon atoms and phenol; more preferred is phenol.

Any molar ratio of phenolic compound to halo-compound which results in formation of the bisphenol is suitable but at least a stoichiometric molar ratio of at least two moles of phenolic compound to halo-compound is preferred, more preferably an excess of the stoichiometric amount of phenolic compound is used. Preferred mole ratios of phenolic compound to halo-compound are from about 2:1 to about 40:1, with about 5:1 to about 25:1 more preferred and from about 5:1 to 15:1 most preferred. These molar ratios are preferred because they increase result in greater yields of bisphenol products and decrease yields of polymeric products formed by reaction of a halo-compound with the reaction product of one mole of chloro-compound with one mole of phenolic compound. Use of a large excess of phenolic compound e.g. greater than about 25:1 is generally less preferred because it is wasteful of phenolic compounds or requires voluminous recycle.

The reaction temperature is preferably from about $-20°$ C. to about $+100°$ C., more preferably from about 20° to about 50° C. most preferably about room temperature. Temperatures above the preferred range can promote undesirable reactions, while those below the range make it difficult to maintain the reaction mass in molten condition (if no solvent is used) or will unduly slow the rate of reaction. Lower temperatures are, however, suitable when a solvent is used, but slower reaction rates are generally observed.

Reaction solvents may include any solvent for the reactants which does not react undesirably with either the reactants or the products under reaction conditions. Preferred solvents include chlorinated aliphatic compounds, e.g. chloroform, carbon tetrachloride, trichloroethylene and the like; aromatic hydrocarbons, e.g. benzene, ethylbenzene and toluene; aromatic ethers such as phenyl ether; and halogenated aromatics such as chlorobenzene. Excess phenolic compound can also serve as a solvent for the reaction. Other useful solvents include tetrahydrofuran, acetic acid and nitriles such as acetonitrile.

Trihalotoluenes and dihalocyanotoluenes are commercially available and can be prepared by means within the skill in the art. The aromatic dihalo-compounds having at least two alpha halogen atoms and at least one beta hydrogen atom, for instance 1,1-dichloroethylbenzene can be made by the chlorination of corresponding halohydrocarbons, for instance 1-chloroethylbenzene, with molecular halogen using a phosphorus halide catalyst, e.g. $PCl_3$ or $PCl_5$, in the presence of light or other initiator (see British patent 1,563,164).

A new and better method of making dihalo-compounds such as 1,1-dichloroethylbenzene is taught in a co-filed application of two of the present inventors in which either organic or inorganic hypochlorites are reacted with ethylbenzene to obtain good selectivity to 1,1-dichloroethylbenzene. The application referred to is "METHOD FOR THE SELECTIVE ALPHA HALOGENATION OF ALKYLAROMATIC COMPOUNDS", U.S. application Ser. No. 472,507 filed Jan. 29, 1990. That application is incorporated herein by reference with respect to the teachings concerning the method of making the dihalo reactant of the present application. A reactive hypohalite compound is reacted with an alkyl aromatic compound having at least one aliphatic substituent and which contains at least two alpha-hydrogens and in which each aliphatic substituent has at least one beta-hydrogen in the presence of a free radical generating medium. Useful hypohalites include alkali metal hypohalites used with phase transfer catalyst and t-alkyl hypohalites such as t-butyl hypochlorite. At least 2 moles of hypohalite is used for each mole of alkylaromatic compound. Useful free radical catalysts include peroxides such as t-butyl peroxide and t-amyl peroxide and hydroperoxides such as chloro-t-butyl hydroperoxide, cumene hydroperoxide and cyclohexane hydroperoxide. Diazo compounds and diacyl peroxides are similarly useful. Representative alkyl aromatic compounds include ethylbenzene, n-propylbenzene, n-butylbenzene, n-octylbenzene, n-decylbenzene, n-dodecylbenzene, ethylphenyl acetate, ethylnaphthalene, diethylbenzene, diethylbiphenyl, n-propylbiphenyl, ethylthiophene and the like.

Dehydrochlorination of 1,1-dichloroethylbenzene or other such dihalo-compounds having a beta hydrogen will produce the corresponding 1-halostyrene which is employed in the process of the present invention for the preparation of the triaromatic bisphenols.

The halo-compound, for instance 1,1-dichloroethylbenzene or 1-chlorostyrene, is added to the molten phenolic compound or, optionally, to the phenolic compound in solution, and reacted at a suitable temperature. The phenolic compound is preferably employed in excess to limit the formation of higher molecular weight phenolics. To form a bisphenol in good yield, the phenolation (reaction of phenolic compound with halo-compound) requires at least two moles of phenolic compound for each mole of the halo-compound.

When the reaction is conducted by reacting a 1-halostyrene, trihalotoluene or dihalocyanotoluene with the phenolic compound the conditions are substantially the same as when using the dihalo-compounds illustrated by 1,1-dichloroethylbenzene. When mixtures of suitable dihalo-compounds, trihalotoluenes, cyanodihalotoluenes and/or 1-halostyrenes are employed, the mole ratios and other conditions and parameters are substantially the same as when using either of these reactants separately.

It is advantageous to avoid water in the reaction between the phenolic compound and the halo-compound because in the presence of acid, the halo-compounds react with water to form acetophenone. Acetophenone, thus, may be present even though it is not a reactant in the process of the invention. To avoid this side-reaction it is preferred to dry or use anhydrous reagents, catalysts and solvents for the reaction. It is also advantageous to maintain an atmosphere inert to the reaction mixture or of catalytic acid such as hydrogen chloride rather than to allow air (with its moisture) to contact the reaction mixture.

The reaction is preferably allowed to proceed to a preselected degree of completion, before recovery of product. Any degree of completion is suitable, but yield is improved by allowing the reaction to produce as much product as the reaction will produce under reaction conditions within convenient length of time. More preferably, a degree of completion corresponding to a yield of at least about 80 percent is preselected. Most preferably, the preselected degree of completion is that corresponding to substantial disappearance of halo-compound, that is disappearance of at least about 90 weight percent of the halo-compound, more preferably of all halo-compound detectable by laboratory means such as gas chromatography.

Methods of recovering product bisphenols from reaction mixtures are within the skill in the art. Conveniently, when there is little excess phenolic compound remaining in the reaction mixture, a crystallization solvent is added to the reaction mixture to precipitate product. Advantageously, when excess phenolic compound is present, it is removed by means within the skill in the art before a crystallization solvent is added to precipitate the product. Convenient crystallization solvents include aromatic hydrocarbons such as toluene, ethylbenzene and chlorobenzene; chlorinated aliphatics such as chloroform and carbon tetrachloride; ketones such as acetone and methyl ethyl ketone; and esters such as diethyl carbonate and mixtures of these solvents. Crystallation is advantageously enhanced by cooling of the reaction mixture before or after addition of the crystallization solvent. Cooling alone is sometimes sufficient to cause precipitation of product without addition of crystallization solvent. Before crystallization hydrogen chloride is optionally, but preferably removed by means within the skill in the art such as distillation.

The process of the invention advantageously produces triaromatic bisphenols having a high percentage of para isomer (the hydroxyl group on a phenyl ring is para to the ring position of attachment of the carbon atom to which the three aromatic groups are attached). The mole ratio of para to ortho isomers is advantageously equal to or greater than at least about 60:40, preferably at least about 75:25, more preferably at least about 90:10, most preferably at least about 95:5. While the process of the invention generally produces products having these high ratios of para to ortho isomers, other methods of preparing the triaromatic bisphenols generally produce products having lower ratios of para to ortho isomers than those ratios produced in the practice of the invention.

The following experiments are representative of the invention:

EXAMPLE 1

Preparation of Bisphenol AP by reacting DCEB and phenol

Anhydrous phenol (3791.2 g, 40.28 mols) is transferred from a nitrogen-padded drum held at 78° C. to a 5-L three-neck flask equipped with thermocouple, magnetic stirring bar, a nitrogen inlet and a 600 mL dropping funnel (vented through a scrubber to neutralize the HCl acid off-gas). A nitrogen atmosphere is maintained throughout the reaction by a continuous flow of nitrogen gas through the nitrogen inlet. The temperature is maintained with a heating mantle. The phenol is allowed to cool to 50° C. and maintained at that temperature with a heating mantle. 1,1-Dichloroethylbenzene (DCEB) (700.2 g, 4.0 mols) is charged to the dropping funnel and addition is begun at a rate that will complete it in about 4 hours. The phenol solution turns bright red immediately upon addition of DCEB and evolution of HCl (hydrochloric acid) begins within a few minutes. The reaction mixture is stirred continually and held at the 50° C. temperature for one hour after the addition is complete. A sample is analyzed by gas chromatography (G.C.) at this time to determine the completeness of the reaction. When completion of the reaction is indicated by disappearance of the peak corresponding to the halocompound (DCEB), a distillation head is placed on the flask and the bulk of the phenol removed at aspirator pressure (ca. 50 mm Hg). The reaction flask is then allowed to cool to room temperature and 2L of CCl$_4$ (carbon tetrachloride) is added with stirring. When this solution is cooled to room temperature and filtered. 904.8 (78% of theoretical yield) of white crystals (m.p. 187–89) are obtained. The crystallized product is bis-1,1-(4'-hydroxyphenyl)-1-phenylethane (4,4'-Bisphenol AP) and contains no detectable bis-1-1-(2,4'hydroxyphenyl)-1-phenylethane (2,4'-Bisphenol AP).

EXAMPLE 2-15

Preparation of bisphenol AP employing different parameters

Other experiments are conducted in the manner of Example 1 employing different temperatures, ratios of phenol to 1,1-dichloroethylbenzene, and other solvents. In some examples, additional HCl is supplied to the reaction mixture by sparging the mixture with HCl to the point of saturation. Conditions of the reactions and the results are shown in Table 1.

TABLE I

| Ex. No. | Ratio of DCEB/ Solvent (weight percent) | Ratio of Phenol/ Solvent (weight percent) | Mol Ratio Phenol/ DCEB | HCl (saturated) | Temp. (°C.) | Mole percent Yield | Mole percent bis-1,1-(4-hydroxyphenyl)-1-phenylethane |
|---|---|---|---|---|---|---|---|
| 2 | /none | /none | 3.6 | no | 43 | 37 | 97.1 |
| 3 | /none | /none | 12.8 | yes | 43 | 80 | 94.6 |
| 4 | /none | /none | 11.6 | no | 43 | 81 | 95.7 |
| 5 | /none | /none | 16.2 | yes | 43 | 77 | 96.8 |
| 6 | /none | /none | 17.7 | no | 43 | 79 | 95.6 |
| 7 | /none | /none | 17.9 | yes | 42–34 | 84 | 97.4 |
| 8 | /none | /THF (79%) | 19.6 | yes | 40 | 57 | 99.0 |
| 9 | /none | /CCl$_4$ (89%) | 11.2 | no | 35 | 71 | 98.2 |
| 10 | /CCl$_4$ (29%) | /none | 18.1 | yes | 40 | 85 | 96.8 |
| 11 | /none | /CCl$_4$ (24%) | 6.4 | no | 27 | 58 | 100 |
| 12 | /none | /CCl$_4$ (66%) | 11.5 | no | 25 | 75 | 97.8 |
| 13 | /CCl$_4$ (18%) | /CCl$_4$ (66%) | 22.6 | yes | 25 | 87 | 97.9 |
| 14 | /CCl$_4$ (18%) | /CCl$_4$ (66%) | 22.6 | yes | 25 | 89 | 98.1 |
| 15 | /CCl$_4$ (18%) | /CCl$_4$ (66%) | 22.6 | yes | 25 | 89 | 98.1 |

EXAMPLES 16 and 17

Preparation of bisphenol AP by reacting αchlorostyrene with phenol

In the manner of Example 1, α-chlorostyrene (α-CS) is substituted for DCEB in the reaction with phenol to make the Bisphenol AP. Conditions and results are shown in Table II.

TABLE II

| Ex. No. | Ratio of α-CS/ solvent (weight percent) | Ratio of Phenol/ solvent (weight percent) | Mol Ratio: Phenol/ α-CS | HCl (saturated) | Temp. (°C.) | % Yield | Mole Percent bis-1,1-(4-hydroxyphenyl)-1phenyl ethane |
|---|---|---|---|---|---|---|---|
| 16 | /none | /none | 15.5 | yes | 43 | 83 | 95.7 |
| 17 | /none | /CCl$_4$ (64%) | 10.2 | yes | 25 | 76 | 97.8 |

EXAMPLE 18

Preparation of bisphenol AP by reacting DCEB and phenol

In yet another preparation, anhydrous molten phenol (4350.6 g, 46.22 moles) and 900 mL CCl$_4$ are placed in a 5-L flask fitted in the manner of Example 1. The mixture is allowed to cool to 30° C. while being sparged with HCl, and DCEB (712.46 g, 4.07 moles) is added dropwise to the stirring mixture over a 5-hour period. The mixture is allowed to stir an additional 45 min. or until G.C. analysis shows the reaction to be complete. Excess phenol is removed by distillation and 2500 mL of chlorobenzene is added with stirring and the mixture is allowed to cool to room temperature. Crystals of product are filtered, and washed with CCl$_4$. After drying in a vacuum oven at 120° C. overnight a 92% yield of bisphenol AP (1105.48 g) is obtained based on the starting DCEB. The product is 99.6% 4,4'-bisphenol AP. The crystallized product contains no detectable 2,4'-bisphenol AP.

EXAMPLE 19

Preparation of bisphenol AP by reacting α-chlorostyrene and phenol in ethylbenzene solvent To a quantity (957.5 g) of phenol at 40° C. is added 115 g of ethylbenzene. Anhydrous HCl is bubbled through the mixture for one hour and used to bring the pressure to 10 psig (68.95 K Pa gauge). The solution is agitated while 201.3 g of α-chlorostyrene in 300 g ethylbenzene is continuously fed into the reaction mixture (one-half over a 5-hour period and the remainder in an additional 7 hour period). The temperature of the reaction mixture is lowered gradually to 32° C. over the first 80 minutes and maintained there for the remainder of the 12-hour reaction period. Analysis of the reaction mixture by liquid chromatography shows a selectivity to bisphenol AP of 91% (98.9% 4,4'-bisphenol AP) based on α-chlorostyrene. The actual yield of product recovered by crystallization is 89% (100% 4,4'-bisphenol AP), based on the α-chlorostyrene.

EXAMPLE 20

Using 1,1,1-Trichlorotoluene to prepare Tris-1,1,1-(4-Hydroxyphenyl)toluene

In a manner of Example 1, benzotrichloride (0.35 moles, 69.0 g) is added to phenol (7.24 moles, 681.4g) dissolved in carbon tetrachloride (2.59 moles, 398.5 g) over a 4 hour period. The reaction mixture turns bright red and vents HCl immediately upon the addition of the first drops of benzotrichloride. The excess phenol is distilled at aspirator vacuum and the product is crystallized from diethylcarbonate. Analysis of proton nuclear magnetic resonance (HNMR) shows peaks from a tetramethylsilane standard of 86.8 (q,12H), 87.1(s,5H), 88.5(s,3H) (q=quartet, s=singlet) corresponding to a structure of tris-1,1,1-(4-hydroxyphenyl) toluene. The melting point is measured as 272-275° C.

We claim:

1. A process for the preparation of an aromatic polyhydroxy compound at least about 60 mole percent of the isomers of which are described as follows

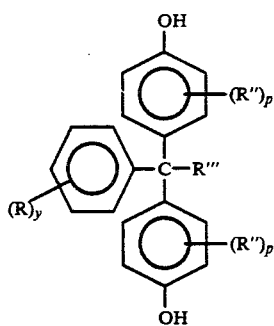

wherein each R or R" is independently an inert substituent or is joined with one or more other R's, one or more other R"'s, or a mixture thereof to form a cycloaliphatic or aromatic group; R''' is —CN, (R")p-phenyl-OH, —CHR'$_2$ or —CH$_2$R'; each R' is independently H or an aliphatic group; y is an integer from 0 to 5; and each p is independently an integer from 0 to 4; said process comprising (a) reacting a phenolic compound with at least one halo compound selected from (i) aromatic dihalo-compounds described as follows

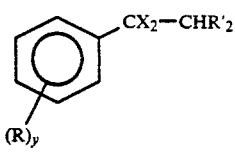

wherein R, R' and y are as set forth above, and each X is independently chlorine or bromine; (ii) halo-styrene compounds described above as follows

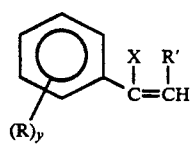

wherein R, R', X and y are as set forth above; and (iii) halotoluene compounds described as follows

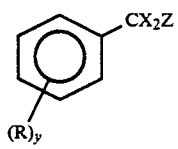

wherein R, X and y are as set forth above, and Z is chlorine, bromine or —CN; at a temperature of about −20° C. to about 100° C. and at greater than atmospheric pressure, where the molar ratio of the phenolic compound to the halo-compound is about 2:1 to about 40:1; and (b) recovering the aromatic polyhydroxy compound.

2. The process of claim 1 wherein the halo-compound is selected from aromatic dihalo-compounds, halo-styrene compounds, halotoluene compounds, and mixtures thereof.

3. The process of claim 2 wherein the phenolic compound is phenol, the halo-compound is selected from 1,1-dichloroethylbenzene, α-chlorostyrene and mixtures thereof, and the aromatic polyhydroxy compound is bis-1,1-(4-hydroxyphenyl)-1-phenylethane.

4. The process of claim 2 wherein the molar ratio of phenolic compound to halo-compound is in excess of the stoichiometric amount.

5. The process of claim 4 wherein the molar ratio of phenolic compound to halo-compound is from 5/1 to about 25/1.

6. The process of claim 2 wherein a solvent is employed.

7. The process of claim 6 wherein the solvent is excess phenol.

8. The process of claim 6 wherein the solvent is a chlorinated hydrocarbon.

9. The process of claim 8 wherein the chlorinated hydrocarbon is a chlorinated aliphatic hydrocarbon having one or two carbons.

10. The process of claim 9 wherein the chlorinated aliphatic hydrocarbon is carbon tetrachloride.

11. The process of claim 6 wherein the solvent is an aromatic hydrocarbon.

12. The process of claim 11 wherein the aromatic hydrocarbon is ethylbenzene.

13. The process of claim 2 wherein the temperature of reaction is maintained at from about 20° C. to about 50° C.

14. The process of claim 2 wherein the halo-compound is added to the phenolic compound.

15. The process of claim 14 wherein an acid catalyst is used.

16. The process of claim 15 wherein the phenolic compound is admixed with a hydrogen halide prior to addition of the halo-compound.

17. The process of claim 15 wherein the acid catalyst is hydrogen chloride.

18. The process of claim 14 wherein the reaction is conducted under a pressure of from about 1 to about 100 atmospheres.

19. The process of claim 18 wherein the pressure is provided by a hydrogen halide.

20. The process of claim 19 wherein the hydrogen halide is hydrogen chloride.

21. The process of claim 2 wherein the structure describes at least 75 mole percent of the isomers of the aromatic polyhydroxy compound.

22. The process of claim 21 wherein the structure describes at least 90 mole percent of the isomers of the aromatic polyhydroxy compound.

23. The process of claim 22 wherein the structure describes at least 95 mole percent of the isomers of the aromatic polyhydroxy compound.

24. The process of claim 2 wherein the halo-compound is a chloro-compound.

25. The process of claim 24 wherein the chloro-compound is selected from 1-chlorostyrene and 1,1-dichloroethylbenzene and mixtures thereof.

26. The process of claim 24 wherein the chloro-compound is a trichlorotoluene or dichlorocyanotoluene, which is unsubstituted or inertly substituted, or mixtures thereof.

27. The process of claim 2 wherein Z is chlorine or bromine and the phenolic compound is phenol.

28. A process for the preparation of bis-1,1-(4-hydroxyphenyl)-1-phenylethane which comprises
   (a) saturating phenol or a solution thereof with anhydrous HCl,
   (b) adding thereto a chloro-compound selected from the group consisting of 1,1-dichloroethylbenzene, α-chlorostyrene and mixtures thereof, the molar ratio of phenol to the chloro-compound being about 2:1 to about 40:1,
   (c) allowing the reaction to proceed, at a temperature of about −20° C. to about 100° C. and at greater than atmospheric pressure, to a preselected degree of completion,
   (d) removing HCl and excess phenol, and
   (e) recovering the desired product.

* * * * *

UNITED STATES PATENT AND TRADEMARK OFFICE
CERTIFICATE OF CORRECTION

PATENT NO. : 5,136,110

DATED : August 4, 1992

INVENTOR(S) : Walters et al.

It is certified that error appears in the above-identified patent and that said Letters Patent is hereby corrected as shown below:

Column 10, line 13, change "compounds described above as follows" to read -- compounds described as follows --.

Signed and Sealed this

Eighteenth Day of January, 1994

Attest:

BRUCE LEHMAN

*Attesting Officer*  *Commissioner of Patents and Trademarks*